United States Patent [19]

Siegmund

[11] Patent Number: 4,598,698
[45] Date of Patent: Jul. 8, 1986

[54] DIAGNOSTIC DEVICE

[75] Inventor: Walter P. Siegmund, Woodstock, Conn.

[73] Assignee: Warner-Lambert Technologies, Inc., Morris Plains, N.J.

[21] Appl. No.: 692,434

[22] Filed: Jan. 17, 1985

Related U.S. Application Data

[63] Continuation of Ser. No. 459,568, Jan. 20, 1983, abandoned.

[51] Int. Cl.4 .............................................. A61B 1/00
[52] U.S. Cl. ........................................ 128/4; 604/26; 604/217
[58] Field of Search ........................................ 128/4–8; 604/26, 37, 75, 18, 119, 146, 217

[56] References Cited

U.S. PATENT DOCUMENTS

| | | | |
|---|---|---|---|
| 2,324,898 | 7/1943 | Anderson | 604/217 |
| 2,478,715 | 8/1949 | Schmitt | 604/217 |
| 3,709,214 | 1/1973 | Robertson | 128/6 |
| 3,730,645 | 5/1973 | Mashakaru et al. | 604/26 |
| 4,146,019 | 3/1979 | Bass et al. | 128/6 |
| 4,281,646 | 8/1981 | Kinoshita | 128/6 |
| 4,343,300 | 8/1982 | Hattori | 128/6 |

FOREIGN PATENT DOCUMENTS 2922571  12/1980  Fed. Rep. of Germany .......... 128/4

Primary Examiner—Edward M. Coven
Assistant Examiner—Max F. Hindenburg
Attorney, Agent, or Firm—R. S. Strickler; A. H. Spencer

[57] ABSTRACT

A diagnostic endoscope useful to make remote examinations and retrievals having a pistol grip which includes a built-in flexible pneumatic bulb.

3 Claims, 7 Drawing Figures

DIAGNOSTIC DEVICE

This is a continuation of application Ser. No. 459,568 filed Jan. 20, 1983 now abandoned.

BACKGROUND OF THE INVENTION

1. Field of the Invention

The present invention relates to diagnostic devices and in particular to endoscopes that are useful to make examinations, inspections and retrievals in remote internal locations in medical and veterinary situations.

2. Description of the Prior Art

A typical prior art scope is illustrated in a Warner-Lambert Company publication entitled "AO Flexible Fiber Optic Small Diameter Veterinary Fiberscope Model VFS-2" 4/81.

This scope includes a pistol grip, a flexible shaft enclosing image and light transmitting fiber optic bundles, deflection means and a retrieval mechanism. The unit also includes a separate tubular element depending from the scope and terminating in a flexible pneumatic bulb operable manually to insufflate the region being observed.

The aforesaid Model VFS-2 scope has the disadvantage that its operation requires use of both hands, that is, one hand to grasp the pistol grip and the other hand to manipulate the separate pneumatic bulb.

Consequently, it is a primary feature of the present invention to incorporate the bulb into the pistol grip. In such an arrangement, an operator can hold the scope by grasping the pistol grip with capability of actuating the pneumatic bulb in one-hand fashion. In this arrangement the second hand is free to manipulate other nearby instrumentalities.

It is a further feature of the present invention to provide a compact pistol grip-bulb package or assembly with a minimum number of appendages dangling from the scope.

A still further feature of the invention is the provision of an endoscope structure which provides the operator with easy single-handed access to the pneumatic bulb without having to grope about with the second hand for its location.

A further feature of the invention is the provision of a valve and conduit system facilitating introduction of fluid into the shaft of the scope where the pneumatic bulb is operable to pressurize the fluid.

SUMMARY OF THE INVENTION

A diagnostic endoscope embracing principles of the present invention and useful for making examinations and retrievals in remote internal locations in medical or veterinary situations may comprise a pistol grip having a cavity, a flexible pneumatic bulb partially received in said cavity and supported by said pistol grip, an operative portion of the bulb projecting outside the cavity making it possible for the user of the scope to manipulate the bulb while grasping the pistol grip in single-handed fashion.

Other features and advantages of the present invention will become more apparent from an examination of the following specification when read in conjunction with the appended drawings, in which;

DESCRIPTION OF PREFERRED EMBODIMENT

Figure 1:
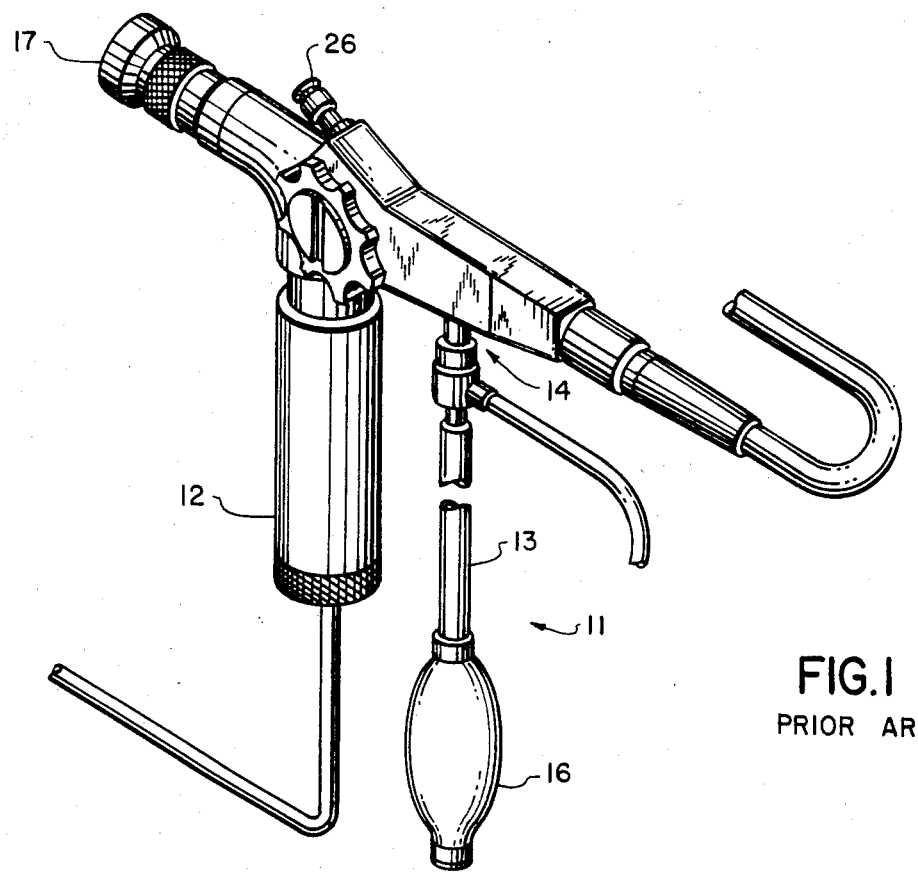
FIG. 1 is an illustration of a typical prior art scope where the pneumatic bulb is separate from the pistol grip.

Referring now to the drawings, the reference numeral 11 designates a prior art endoscope having a pistol grip 12 and a pneumatic tube 13 connected to the scope at 14 and terminating in a flexible pneumatic bulb 16.

In operation of the prior art scope 11, eyepiece 17 is held close to the viewer's eye by grasping the pistol grip in one hand. In operating this prior art scope, a viewer must grope about with his free hand to locate the dangling bulb 16.

Figure 2:
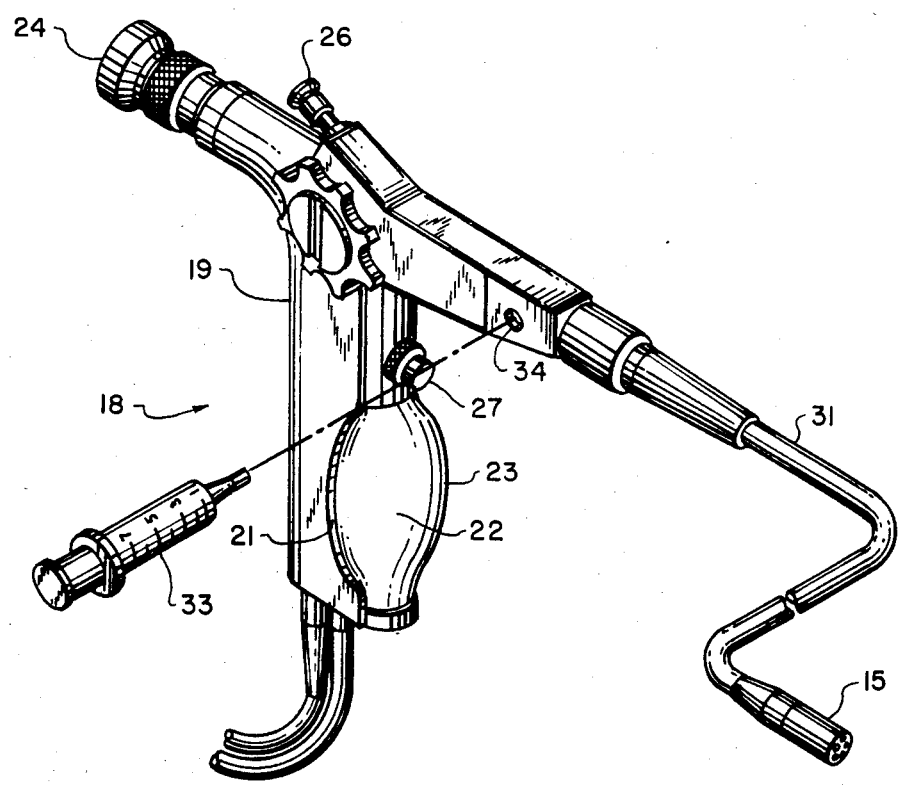
FIG. 2 is a perspective view illustrating the improved scope.

In contrast, a reference to FIG. 2 discloses an improved scope indicated generally at 18 having a pistol grip 19 formed with a recess 21 for receiving and supporting a pneumatic bulb 22.

A substantial portion 23 of the bulb extends beyond the pistol grip and extends beyond the cavity making it possible for the user of the scope to manipulate (compress or relax) the flexible bulb, as desired, using digits of the same hand with which one grasps the pistol grip.

It is noted that the scope includes an eyepiece 24, a channel entry 26 for a retrieval instrument (not shown), a vacuum conduit 5, a light guide 10, a tip deflector wheel 36 and an operating button 27 for applying a vacuum to the region under examination through conduit 5.

Figure 7:
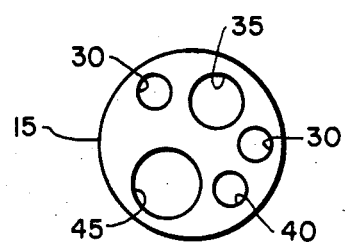
FIG. 7 is a schematic drawing of a typical working end of an endoscope shaft.

FIG. 7 shows the face of the working end 15 of the scope of FIG. 2 including, typically, one or more channels for bundles 30—30 of light transmitting fiber optics, a channel for an image bundle 35, a combined insufflation-irrigation channel 40 and vacuum or biopsy channel 45.

Note that all valves disclosed are of the ball check variety held normally closed or open, as the case may be, by a spring such as a coil spring in well-known fashion. Obviously the selection of check valve structure is purely a matter of engineering choice which can be made freely without departing from the spirit and scope of the invention.

Referring now to FIGS. 3, 4, 5 and 6, the valve and conduit system operates as follows:

Assume that the bulb 22 is in the normal extended condition filled with air. In this condition, check valve 28 is normally closed to the atmosphere.

Figure 3:
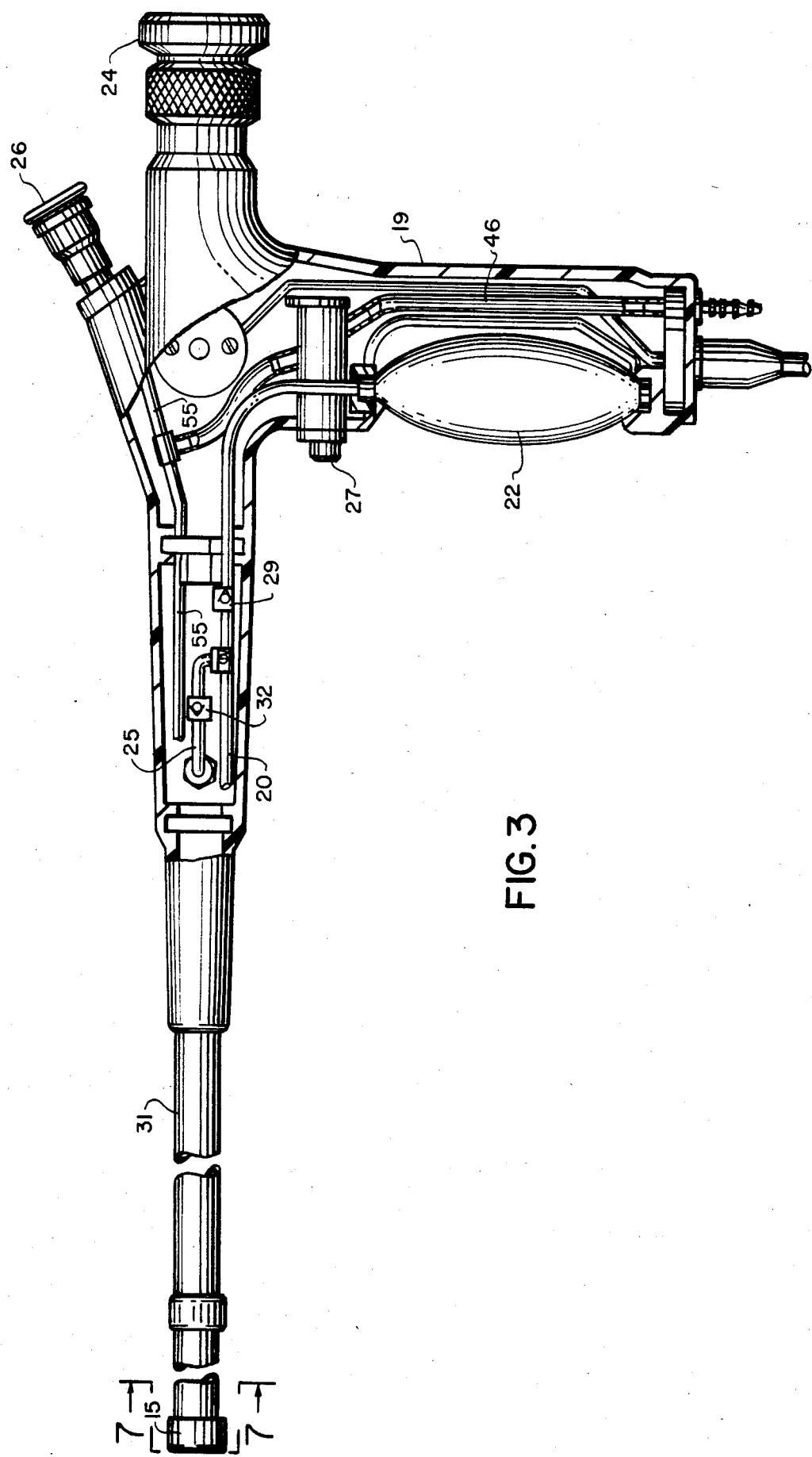
FIG. 3 is a side view of FIG. 2 with certain portions broken away to show the disposition of valves and conduits.
Figure 4:
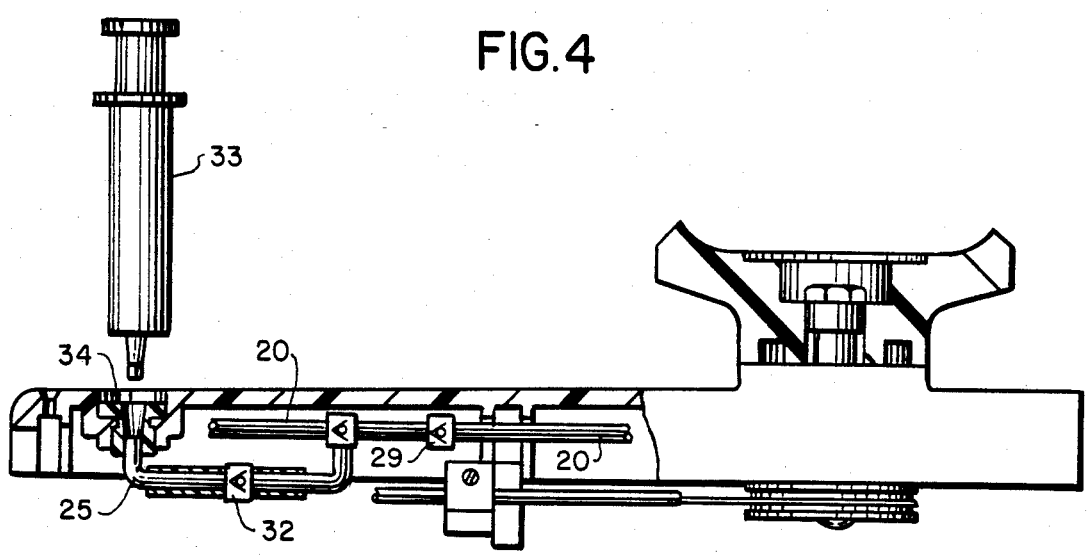
FIG. 4 is a top plan view of FIG. 3 with portions broken away to show the valves and conduits for introducing irrigation fluid.
Figure 5:
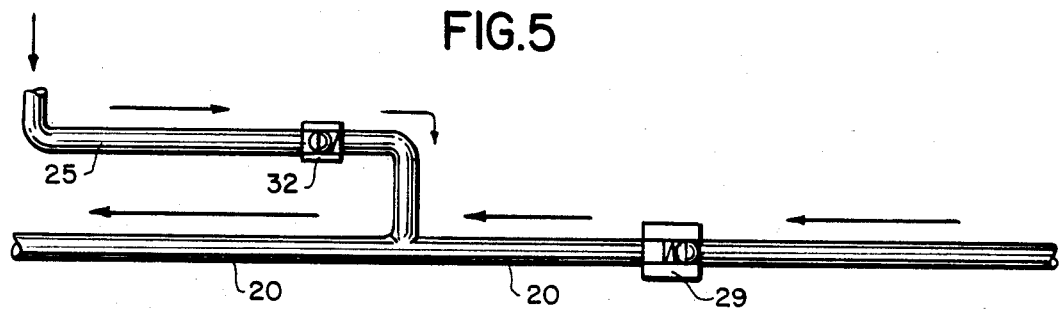
FIG. 5 is a schematic drawing showing valve positions during insufflation.
Figure 6:
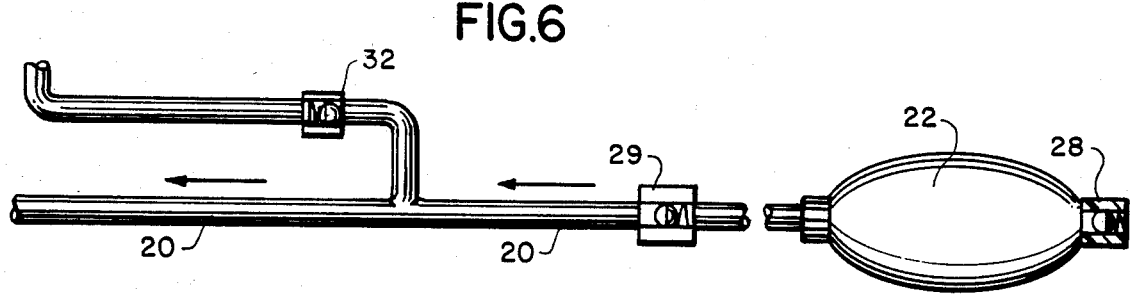
FIG. 6 is a schematic drawing showing valve positions during irrigation.

Upon manual compression of the bulb 22, air pressure opens normally closed check valve 29 and air flows through conduit 20 introducing air under pressure into shaft 31 and exhausting at shaft face 15 through channel 40 (FIGS. 2, 3 and 7). Note that check valve 32 is normally closed blocking passage of air through conduit 25 leading to a syringe socket 34 (FIGS. 2 and 4).

Upon relaxation of the bulb 22, check valve 29 returns to its normally closed position and the natural tendency for the bulb to draw a vacuum opens check valve 28 introducing a new volume of air into the bulb. Sequential compression and relaxation of the bulb will "pump" air to the shaft face 15, as desired.

In the event it is desired to introduce fluid into the shaft 31 for irrigation or purging at the face 15, a conventional syringe 33, loaded with suitable fluid, is introduced into syringe socket 34. Upon pumping the syringe, fluid flows through conduit 25, normally closed check valve 32 is blown open and fluid backs into conduit 20 up to normally closed valve 29 and flow occurs through conduit 20 and discharges at the face 15 of the shaft 31 through channel 40. (See FIGS. 4, 6 and 7.)

If desired, the fluid introduced by the syringe 33 may be pressurized beyond that created by the syringe by merely actuating the pneumatic bulb 22 in the fashion previously described.

That is, with a charge of fluid introduced into the conduit 20, removal of the syringe permits check valve 32 to return to its normally closed position retaining the fluid in the system. Thereafter, compression of bulb 22 applies air pressure to conduit 20 and to the fluid within bringing about irrigation or purging at the face 15 of shaft 31 exhausting through channel 40.

Fluid is removed by applying a vacuum to conduit 55 (FIG. 3). The vacuum is derived from a remote vacuum pump (not shown) through conduit 46 and is applied by depressing vacuum operating button 27 drawing a vacuum through conduit 55 and conduit 46; conduit 55 is sealed to the atmosphere by a check valve at 26 (not shown).

It is to be noted in particular that the incorporation of the flexible pneumatic insufflation bulb into the scope pistol grip permits a scopist to manipulate the bulb, the tip deflector wheel and the vacuum button with the digits (including the thumb) of the same hand with which the pistol grip is grasped.

Thus, the scopist's other hand is free to manipulate the syringe, or to insert a biopsy forcep into channel entry 26 or to attend to any other procedure or detail with ease.

It is anticipated that a wide variety of embodiments of this invention may be devised without departing from the spirit and scope thereof.

What is claimed is:

1. In an endoscope useful for examinations and retrievals in remote internal locations in medical or veterinary situations where the scope includes a pistol grip and a flexible pneumatic bulb, the improvement comprising:

a cavity formed in the pistol grip for receiving and enclosing a top and bottom end of the bulb while leaving the middle of the bulb exposed, said cavity having a top portion and a bottom portion, said bulb top end defining a discharge end and said bottom defining an inlet end, the ends of said bulb being secured to complementary top and bottom portions of said cavity whereby the middle of the bulb is operable by the digits of a pistol-gripping hand.

2. The improvement recited in claim 1 in which the cavity includes a substantially continuous concave surface and said portion of said bulb is in substantial areal contact with the concave surface of said cavity.

3. In an endoscope useful for examinations and retrievals in remote internal locations in medical or veterinary situations where the scope includes a pistol grip supporting a vacuum operating button and a flexible pneumatic bulb, the improvement comprising:

a cavity formed in the pistol grip for receiving and enclosing a portion of the bulb, said cavity having a top portion and a bottom portion, said bulb having a top defining a discharge end, a bottom defining an inlet end and a middle portion, the ends of said bulb being secured to complementary top and bottom portions of said cavity whereby said middle portion of said bulb and the vacuum operating button are both operable by the digits of a pistol-gripping hand.

* * * * *